(12) United States Patent
Zhang et al.

(10) Patent No.: US 8,703,294 B2
(45) Date of Patent: Apr. 22, 2014

(54) BIOACTIVE GRADED ZIRCONIA-BASED STRUCTURES

(75) Inventors: Yu Zhang, Chatham, NJ (US); Racquel Legeros, New York, NY (US); Jae-Won Kim, Elmhurst, NY (US)

(73) Assignee: New York University, New York, NY (US)

( * ) Notice: Subject to any disclaimer, the term of this patent is extended or adjusted under 35 U.S.C. 154(b) by 398 days.

(21) Appl. No.: 12/284,620

(22) Filed: Sep. 22, 2008

(65) Prior Publication Data

US 2009/0118114 A1 May 7, 2009

Related U.S. Application Data

(60) Provisional application No. 60/994,833, filed on Sep. 21, 2007.

(51) Int. Cl.
| | |
|---|---|
| B32B 17/06 | (2006.01) |
| B32B 15/00 | (2006.01) |
| B32B 9/00 | (2006.01) |
| B32B 19/00 | (2006.01) |
| B05D 1/36 | (2006.01) |
| B05D 3/00 | (2006.01) |
| B05D 3/02 | (2006.01) |
| B05D 1/18 | (2006.01) |

(52) U.S. Cl.
USPC ........... 428/432; 428/426; 428/689; 428/697; 428/698; 428/699; 428/701; 428/702; 427/258; 427/269; 427/273; 427/314; 427/372.2; 427/376.2; 427/419.2; 427/430.1; 427/443.2

(58) Field of Classification Search
USPC ......... 428/426, 428, 432, 689, 697, 698, 699, 428/701, 702; 443/228.1; 427/258, 269, 427/273, 314, 372.2, 376.2, 419.2, 430.1, 427/443.2
See application file for complete search history.

(56) References Cited

U.S. PATENT DOCUMENTS

| | | | |
|---|---|---|---|
| 6,306,925 B1 * | 10/2001 | Clupper et al. ............... | 523/113 |
| 6,641,893 B1 | 11/2003 | Suresh et al. | |
| 7,858,192 B2 * | 12/2010 | Zhang et al. .................. | 428/432 |
| 7,871,706 B2 * | 1/2011 | Zhang et al. .................. | 428/432 |
| 2003/0029910 A1 * | 2/2003 | Goretta et al. ............. | 228/248.1 |

FOREIGN PATENT DOCUMENTS

| | | |
|---|---|---|
| CN | 1 080 627 A | 4/1994 |
| JP | 2006 068249 | 3/2006 |

OTHER PUBLICATIONS

Kim et al., "Calcium phosphates and glass ocmposite coatings on zirconia for enhanced biocompatibility", vol. 25, No. 18, 2004, pp. 4203-4213.*
Hench et al., Science 2002, 295(5557):1014-7.
Liu et al., 2004, 47(3-4):49-121.

(Continued)

*Primary Examiner* — Jonathan Langman
(74) *Attorney, Agent, or Firm* — Klauber & Jackson LLC

(57) ABSTRACT

The present invention provides a functionally graded bioactive glass/ceramic composite structure or bioactive glass/ceramic/bioactive glass sandwich structure for use in such applications as damage resistant, ceramic dental implants, immediate tooth replacement, endodontic posts, orthopedic prostheses, orthopedic stems, bone substitutes, bone screws, plates, and anchors, nonunion defects repair, alveolar ridge augmentation, missing small bone parts (e.g. fingers, toes, etc), maxilla facial reconstruction, spinal fusion, and scaffolds for bone regeneration, comprising a residual bioactive glass or glass-ceramic layer at all accessible surfaces, followed by an underlying graded glass-ceramic layer, and then an dense interior ceramic. Further, the invention provides methods for making the same structure.

13 Claims, 3 Drawing Sheets

(56) References Cited

OTHER PUBLICATIONS

Hench et al., *Journal of Biomedical Materials Research* 1971;5:117-41.
LeGeros, *Monogr Oral Sci* 1991, 15:1-201.
Inuzuka et al., *Solid State Ionics* 2004, 172(1-4):509-513.
Moon et al., *Eco-Materials Processing & Design VI* 2005, 486-487:101-104.
Sun et al., *J Biomed Mater Res* 2001, 58(5):570-92.
Hench et al., *An Introduction to Bioceramics*. 1993.
Black J., *J Biomed Mater Res* 1976, 10(4):503-9.
Ferraris et al., *Biomaterials* 2000, 21(8):765-73.
Lacefield et al., *Biomaterials* 1986, 7(2):104-8.
Gomez-Vega et al., *Advanced Materials* 2000, 12(12):894-898.
Gomez-Vega et al., *Journal of Dental Research* 1998, 77:108-108.
Foppiano et al., *Acta Biomaterialia* 2006, 2(2):133-142.
Huang et al., *J Mater Sci Mater Med* 2007, 18(1):57-64.
Suresh et al. (1997) *Acta Materialia* 45(4): 1307-21.
Jitcharoen et al. (1998) *Journal of the American Ceramic Society* 81(9): 2301-8.
Suresh et al. (1999) *Acta Materialia* 47(14): 3915-3926.
Kobayashi et al., *Solid State Ionics* Aug. 3-4, 1981:489-493.
Hirano, *British Ceramic Transactions and Journal* 1992, 91(5):139-147.
Piconi et al., *Biomaterials* 1999, 20(1):1-25.
Zhang et al., *Journal of Biomedical Materials Research* 2004, 71B(1):166-71.
Piascik et al., *Journal of Vacuum Science & Technology* A 2006, 24(4):1091-1095.
Hench, *Science*; 1984, 226:630-636.
LeGeros, et al., Journal of Material Science 39 (2004) 5577-5579.

* cited by examiner

BIOACTIVE GRADED ZIRCONIA-BASED STRUCTURES

CROSS REFERENCE TO RELATED APPLICATIONS

The present application claims the benefit under 35 U.S.C. §119 of U.S. Provisional Application Ser. No. 60/994,833 filed Sep. 21, 2007, the contents of which are hereby incorporated by reference.

FIELD OF THE INVENTION

The present invention relates to dental and orthopedic implants and related devices, and methods for producing the same with improvements in functionalities (e.g. bioactivities and esthetics) and damage resistance using functionally graded materials ("FGMs") such as a functionally graded calcium phosphate-based glass/zirconia (CPG/Z) or CPG/Z/CPG sandwich material.

BACKGROUND OF THE INVENTION

Biomaterials are permanently or temporarily used to repair or replace missing or diseased parts of the human body (e.g. joint replacements, contact lenses, heart valves, vascular prostheses, dental implants, etc). Ultimately, almost every human in technologically advanced societies will host a biomaterial.

Ceramics are extremely popular in medical and dental applications because of their strength, chemical inertness, wear resistance, and esthetics. However, the full potential of ceramics in biomedical applications has not been realized, with biointergration and/or strength being the major concerns. The strong ceramics such as zirconia and alumina are bioinert and possess high elastic modulus. The bioinert property prevents the formation of chemical bonds with the surrounding tissues. The high elastic modulus results in stress shielding of the hard tissue, leading to local bone resorption. The bioactive ceramics (e.g. calcium phosphate ceramics, bioglasses) are able to form strong chemical bonds with adjacent tissues and exhibit comparable modulus to hard tissues (bone, enamel, or dentin). Unfortunately, bioactive ceramics are relatively weak and thus structurally unstable.

The initial applications of ceramics in medicine are based on their chemical inertness and wear resistance. (Hench et al., Science 2002, 295(5557):1014-7) However, the inert surface fails to form biochemical bonds with the surrounding tissues, often leading to implant loosening. In addition, the high elastic modulus of the strong, bioinert ceramics (often an order of magnitude higher than that of hard tissues) results in stress shielding of the surrounding bone, leading to local bone resorption. (Liu et al., 2004, 47(3-4):49-121) The development of the bioactive ceramics in the late 1960s and early 1970s (e.g. calcium phosphate ceramics, silica-based bioactive glasses and glass ceramics) allow their use where bonding to hard tissues is needed. (Hench et al., Journal of Biomedical Materials Research 1971; 5:117-41; LeGeros, Monogr Oral Sci 1991, 15:1-201).

In addition, the bioactive ceramics have a relatively low modulus (on the same order of hard tissues) and therefore do not have a significant stress shielding problem. However, the bioactive ceramics exhibit relatively low strength and fracture toughness, and thus they are not suitable for load bearing applications (e.g. dental and orthopedic implants).

Public demands in biological compatibility and esthetics have driven the increasing popularity of ceramics as the materials of choice for dental and orthopedic implant devices. Dental and orthopedic implants bear load during function, requiring strong ceramics. However, strong ceramics such as zirconia and alumina are bioinert, failing to form strong bonds with vital tissues. In addition, strong alumina and zirconia ceramics possess high modulus of elasticity, resulting in local bone resorption. Both the bioinertness and high modulus can lead implant loosening and failure. On the other hand, the low modulus, bioactive ceramics are relatively weak and thus structurally unstable.

The current approaches to this problem are to either make a composite consisting of both inert and active phases, e.g., mixed hydroxyapatite (HA) and zirconia or alumina, or to coat the surface of a strong and inert ceramic with a bioactive but weak layer (e.g., plasma-sprayed HA coated implants, bioglass coated implants). (Inuzuka et al., Solid State Ionics 2004, 172(1-4):509-513; Moon et al. Eco-Materials Processing & Design Vi 2005, 486-487:101-104; Sun et al., J Biomed Mater Res 2001, 58(5):570-92). Compared to their parental materials, the composites exhibit a moderate bioactivity and strength. On the other hand, the bioactive ceramic coatings on the biologically inert ceramic are likely to undergo delamination and fracture due to the coating/substrate bonding issue, coefficient of thermal expansion (CTE) mismatch, and the abrupt change in physical and mechanical properties at the coating/substrate interface.

Coating of inert materials with bioactive glasses dates to the mid 1970s, with a primary effort in modifying the surface of metallic orthopedic stems and dental implants for better bone integration. (Hench et al., An Introduction to Bioceramics. 1993). The strong, tough metallic substrate provides structural support to the weak, brittle bioglass coating, while the bioglass coating protects the surrounding tissues from corrosion products of the metal core which may induce systemic effects. (Black J., J Biomed Mater Res 1976, 10(4):503-9). The problem of obtaining a bioactive glass coating with high mechanical integrity is the chemical reactivity of this type of glass. (Hench et al., An Introduction to Bioceramics. 1993). Silicate-based bioactive glasses contain less than 60 mol % $SiO_2$, and thus exhibit a random two-dimensional sheet-like network structure with many open pathways for ion transport. The open network structure facilitates the rapid formation of a calcium hydrocarbonate apatite layer at the glass surface, which provides binding sites to bone or soft tissue. However, it is also this open network structure that provides pathways for other cations, such as Fe, Cr, Ni, Co, Mo, Ti, or Ta, to migrate from the metal substrate to the glass surface. The presence of these cations at the glass surface inhibit or eliminate the bioactivity of the glass by preventing formation of the HA layer.

Since oxide ceramics are chemically more stable and biologically more compatible than metals and alloys, attempts have been made to coat structural oxide ceramics, such as alumina and zirconia, with bioglasses. (Greenspan et al., J Biomed Mater Res 1976, 10(4):503-509; Ferraris et al. Biomaterials 2000, 21 (8):765-73). The major problem with these systems is a large difference in CTE: the silicate-based bioglasses have a CTE ranging between $12-16\times10^{-6}$, while alumina and zirconia have CTE values of $8\times10^{-6}$ and $10.5\times10^{-6}$, respectively. The high CTE value of bioglass places the coating in tension, which further weakens the bioglass coating. One solution to the above mentioned problems is to utilize two layers of glass coatings. One laboratory developed two layer coatings for Co—Cr—Mo alloy and alumina substrates, and another laboratory exploited multilayer coatings for titanium alloy. (Lacefield et al., *Biomaterials* 1986, 7(2): 104-8; Gomez-Vega et al., *Advanced Materials* 2000, 12(12): 894-898)

For example, recent reports of using silica-based bioactive coating on titanium alloy ($Ti_6Al_4V$) implants show improved bioactivity compared to the original $Ti_6Al_4V$ surface. (Gomez-Vega et al., *Journal of Dental Research* 1998, 77:108-108). However, adhesion of the silica-based bioglass coatings on $Ti_6Al_4V$ surfaces relies on the silica content. A high silica content forms a better bond with the $Ti_6Al_4V$ surface, but also sacrifices the bioactivity of the glass coating. Therefore, multiple coating layers are required to grade the silica content in order to retain the necessary surface bioactivity and a sufficient interfacial bond with the $Ti_6Al_4V$ substrate. Even then, cracks may be observed in the outer bioactive glass layer due to a large CTE mismatch between the glass coatings and $Ti_6Al_4V$ substrate. One in vitro study revealed that the Ca, P-rich surface layer separated from the underlying glass due to the degradation of the silica network in bioglass. (Foppiano et al., *Acta Biomaterialia* 2006, 2(2):133-142). In addition, the silica based bioglass upon dissolution produce a basic environment (pH approximately 9-11), hindering tissue integration. CPG is chemically more stable (due to the absence of silica) and biologically more active (chemically more close to hard tissues) than silica-based bioglass.

Despite significant improvements that have been made to bond bioglass coating to metals and ceramics, widespread application of bioglass coated dental and orthopecdic implants has failed because of the fracture of glass coatings, making them poor candidates for load bearing applications.

It would be useful to create a functionally graded CPG/Y-TZP system with a low modulus, bioactive surface and yet a flexural strength similar to, or even greater than Y-TZP for dental and orthopedic implants. The osteoconductive CPG coating promotes a rapid osteointegration and prevents micromotion at the implant/tissue interface, while the graded CPG/Y-TZP structure retains excellent contact and flexural damage resistance. In addition, the residual outer surface CPG layer acts as an encapsulation layer, preventing hydrothermal degradation of Y-TZP interior, and can be further transformed to a carbonate apatite (CHA) layer by immersing in calcifying solution or simulated body fluid (SBF) with an electrolyte composition similar to that of serum since in all bioactive materials (e.g., calcium phosphates, bioactive glass, calcium sulfates, etc), the newly formed bone is directly attached to a CHA layer. Knowledge generated from this investigation can readily be extended to development of next-generation, strong ceramic scaffolds for medical applications, foreshadowing an array of engineering applications.

SUMMARY OF THE INVENTION

The present invention provides a functionally graded bioactive glass/ceramic composite structure or a bioactive glass/ceramic/bioactive glass sandwich structure for use in such applications as damage resistant, ceramic dental implants, immediate tooth replacement, endodontic posts, orthopedic prostheses, orthopedic stems, bone substitutes, bone screws, plates, and anchors, nonunion fractures repair, alveolar ridge augmentation, missing small bone parts (e.g. fingers, toes, etc), maxilla facial reconstruction, spinal fusion, and scaffolds for bone regeneration comprising an outer residual bioactive glass layer, an underlying graded glass-ceramic layer, and an dense interior ceramic. In some embodiments, the outer residual bioactive glass layer can be further transformed to a carbonate apatite (CHA) layer by immersing in calcifying solution or simulated body fluid (SBF) with electrolyte composition similar to that of serum. In other embodiments, the interior ceramic comprises yttria-tetragonal zirconia polycrystal (Y-TZP) or ceria stabilized tetragonal zirconia polycrystal (Ce-TZP) or magnesia stabilized zirconia (Mg-PSZ) or calcia stabilized zirconia (Ca-PSZ) or alumina or zirconia-alumina composites. Additionally, in some preferred embodiments, the bioactive glass composition powder is dispersed in an aqueous based solution. In other preferred embodiments, the bioactive glass compositions are deposited to accessible surfaces of the ceramic substrate using a solution-precipitation method. In yet further preferred embodiments, the bioactive glass powder (CPG) of the composition contains CaO, $P_2O_5$, MgO, ZnO, $K_2O$ with or without F and with or without additional compounds like borates, yttrium, zirconium, etc. The bioactive glass powder of the composition may in some embodiments be a hybrid of CPG and silica-based glass (SG), CPG/SG with added $SiO_2$. Also, the CTE of the bioactive glass may be closely matched with yttria-tetragonal zirconia polycrystal (Y-TZP) or cerium stabilized tetragonal zirconia polycrystal (Ce-TZP) or magnesia stabilized zirconia (Mg-PSZ) or calcia stabilized zirconia (Ca-PSZ) or alumina or zirconia-alumina composites.

The CPG-based bioactive glass formulation preferably has a Ca/P ratio of about 0.2 to 1.2, preferably 0.4 to 1.0, or 0.5 to 0.8, and in some embodiments about 0.6 and an elastic modulus of approximately 20-80 GPa, preferably 30-70 GPa, or 35-60 GPa, and in some embodiments about 45 GPa. Further in some embodiments, the CPG has a melting temperature of about 400 to 1500° C., preferably about 500 to 1400° C., 600 to 1300° C., or about 700 to about 1250° C. The CPG has a CTE of approximately $50 \times 10^{-7}$ in/in/° C. to approximately $150 \times 10^{-7}$ in/in/° C., or about 75 to about $125 \times 10^{-7}$ in/in/° C., and in some embodiments about 80 to $110 \times 10^{-7}$ in/in/° C. The CPG is infiltrated into the surface of a strong ceramic substrate. The surface of the ceramic substrate consists of a residual CPG layer preferably approximately 1-50 μm, more preferably about 5-40 μm, more preferably about 8-30 μm, and most preferably about 10-20 μm, and a graded CPG/ceramic layer preferably approximately 25-500 μm thick, more preferably about 50-250 μm, and most preferably about 75-150 μm, and a dense ceramic interior. In many embodiments, the CTE of the CPG composition is closely matched with that of the ceramic substrate. That is, the CTE of the CPG and the substrate may be within about 10% or even 5% or 1% of each other.

In a second aspect, the present invention provides a method for preparing a functionally graded bioactive glass/ceramic or functionally graded bioactive glass/ceramic/bioactive glass comprising: (a) applying a powdered bioactive glass composition to accessible surfaces of a partially sintered ceramic substrate thereby covering the ceramic substrate surfaces with a layer of the composition; and (b) infiltrating the bioactive glass composition into the substrate and densifying the substrate by heating the substrate. In some embodiments, the heating is performed to approximately the sintering temperature of the substrate. In other embodiments, the coefficient of thermal expansion (CTE) of the bioactive glass and the coefficient of thermal expansion (CTE) of the substrate material are substantially the same. That is, when the CTEs are substantially the same, the CTE of the bioactive glass and the CTE of the ceramic substrate are within about 50%, 40%, 30%, 25%, 20%, 10%, 5%, 2%, 1% or even 0.5% or 0.25% of each other. In some embodiments, the functionally graded bioglass/ceramic composite bioglass/ceramic/bioglass structure is substantially non-susceptible to warppage or bending and exhibits no significant long-range residual thermal stresses.

In some embodiments, the partially sintered ceramic substrate comprises yttria-tetragonal zirconia polycrystal (Y-TZP) or ceria stabilized tetragonal zirconia polycrystal (Ce-TZP) or magnesia stabilized zirconia (Mg-PSZ) or calcia stabilized zirconia (Ca-PSZ) or alumina or zirconia-alumina composites. In other embodiments, the partial dense substrate is presintered at a temperature of from about 900° C. to about 1700° C. Additionally, in some preferred embodiments, the bioactive glass composition powder is dispersed in an aqueous based solution. In yet further preferred embodiments, the bioactive glass powder of the composition contains CaO, $P_2O_5$, MgO, ZnO, $K_2O$ with or without F and with or without additional compounds like borates, yttrium, zirconium, etc. The bioactive glass powder of the composition may in some embodiments be a hybrid of CPG and silica-based glass (SG), CPG/SG with added $SiO_2$.

In some embodiments, the bioactive glass compositions are deposited to accessible surfaces of partially sintered ceramic substrate using a solution-precipitation method. Partially sintered ceramic substrates are immersed in solutions containing Ca and/or P, and optionally one or more other ion such as, for instance, Mg, Zn, K, optionally F and optionally Zr. In some embodiments, deposition is carried out at room temperature. In other embodiments, deposition is carried out in a conventional oven at temperatures preferably between 40-300° C. for various durations. In yet other embodiments, deposition is facilitated using a microwave method. Infiltration of the bioactive glass composition into the substrate and densifying the substrate may be achieved by heating the substrate to its sintering temperature. In some embodiments, the CTE of the bioactive glass and the CTE of the substrate material are substantially the same. That is, the CTE of the bioactive glass and the substrate are within about 10% or 5% or 1% or 0.5% or even 0.1% of each other.

In a third aspect, the present invention provides a method for preparing a functionally graded bioactive glass/ceramic or functionally graded bioactive glass/ceramic/bioactive glass comprising applying a powdered bioactive glass composition to accessible surfaces of a dense ceramic substrate thereby substantially covering the ceramic substrate surfaces with a layer of the composition. In some embodiments, the bioactive glass composition is deposited to one or more accessible surfaces of a dense ceramic substrate using a solution-precipitation method. A dense ceramic substrate may be immersed in a solution containing Ca and P, and optionally one or more other ions such as, for instance Mg, Zn, and K, optionally F and optionally Zr. In some embodiments, deposition is performed at room temperature. In other embodiments, deposition is performed in a conventional oven at a temperature of, for instance, between 40-300° C. for various durations. In yet other embodiments, deposition may be facilitated using a microwave method. The CTE of the bioactive glass composition is preferably substantially the same as the CTE of the substrate material (i.e. Y-TZP or Ce-TZP or Mg-PSZ or Ca-PSZ or alumina or zirconia-alumina composites).

In some embodiments, the dense ceramic substrate comprises yttria-tetragonal zirconia polycrystal (Y-TZP) or ceria stabilized tetragonal zirconia polycrystal (Ce-TZP) or magnesia stabilized zirconia (Mg-PSZ) or calcia stabilized zirconia (Ca-PSZ) or alumina or zirconia-alumina composites. In other embodiments, the dense substrates are sintered at their respective sintering temperatures.

In some embodiments, infiltrating the bioactive glass composition into the dense substrate is performed in one or more firing cycles at a temperature of from about 600° C. to 1700° C., or 700° C. to 1500° C., preferably from about 750° C. to 1400° C. The functionally graded bioactive glass/ceramic composite or graded bioactive glass/ceramic/bioactive glass structure is preferably substantially non-susceptible to warpage and bending and preferably exhibits no significant long-range residual thermal stresses. The functionally graded bioactive glass/ceramic composite or graded bioactive glass/ceramic/bioactive glass structure may be produced in some instances by the methods described herein.

The present invention provides methods for preparing functionally graded bioactive glass/ceramic or bioactive glass/ceramic/bioactive glass structures for use in such applications as bioactive, damage resistant, ceramic dental implants, immediate tooth replacement, endodontic posts, orthopedic prostheses, orthopedic stems, bone substitutes, bone screws, plates, and anchors, nonunion fractures repair, alveolar ridge augmentation, missing small bone parts (e.g. fingers, toes, etc), maxilla facial reconstruction, spinal fusion, and scaffolds for bone regeneration whereby the surface bioactive glass or glass-ceramic layer may be further transformed to a carbonate apatite (CHA) layer by immersing in a calcifying solution or simulated body fluid (SBF) having an electrolyte composition similar to that of serum. In all bioactive materials (e.g., calcium phosphates, bioactive glass, calcium sulfates, etc), the newly formed bone is directly attached to a CHA layer.

In some embodiments, the glass of the composition has a CTE approximately matching that of the substrate material. In preferred embodiments, the substrate comprises yttria-tetragonal zirconia polycrystal (Y-TZP) or cerium stabilized tetragonal zirconia polycrystal (Ce-TZP) or magnesia stabilized zirconia (Mg-PSZ) or calcia stabilized zirconia (Ca-PSZ) or alumina or zirconia-alumina composites.

DETAILED DESCRIPTION OF THE INVENTION

As used herein, the following terms mean as follows: By "a functionally graded bioactive glass/ceramic structure" is meant a bioactive surface consisting predominantly of a glassy phase, followed by an underlying layer that gradually becomes more densely packed with a ceramic and eventually becomes a pure, dense ceramic structure.

By "bioactive" is meant a property of a material that allows direct bonding with bone thus providing a uniquely strong bone-material interface.

By "bioactive glass composition" is meant an appropriate combination of CaO, $P_2O_5$, MgO, ZnO, $K_2O$ with or without $CaF_2$ or with or without zirconia that imparts a 'bioactive' quality.

By "presintered" is meant that a powdered composition of a substrate has been subjected to an elevated temperature/time heating schedule below a sufficient temperature for a sufficient time that would effect full densification of the compound.

Figure 1:
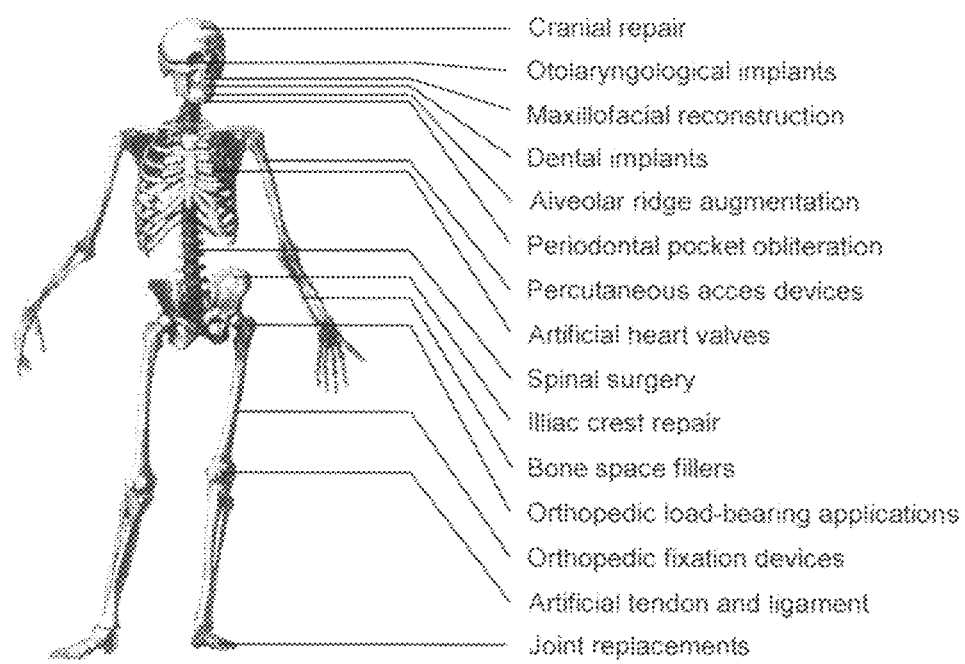
FIG. 1 depicts some of the clinical uses of ceramics. Ceramics are extremely popular in medical and dental applications because of their strength, chemical inertness, wear resistance, and esthetics.
Figure 2:
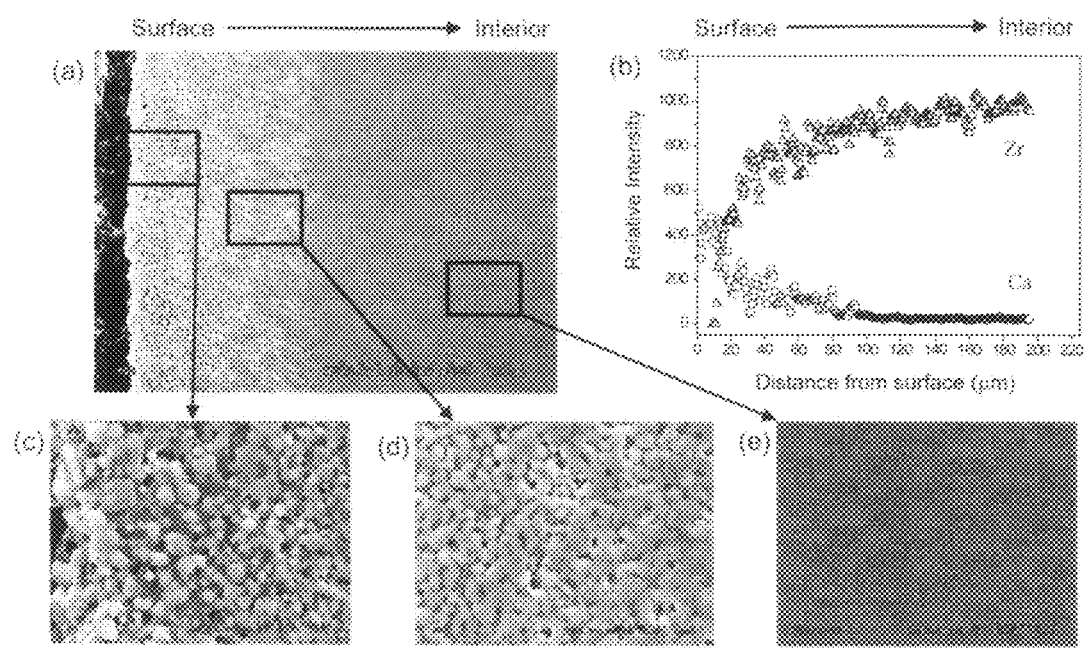
FIG. 2. SEM of functionally graded materials (FGM) rod section consisting of (a) CPG infiltrated Y-TZP (low magnification view); (b) Energy dispersive X-ray line mapping from surface to interior, revealing a gradual transition in Ca and Zr contents. Higher magnification SEM images showing: (c) gradual transition from the surface residual CPG (left) to the graded CPG/Y-TZP structure (right); (d) graded CPG/Y-TZP region; and (e) dense Y-TZP interior.
Figure 3:
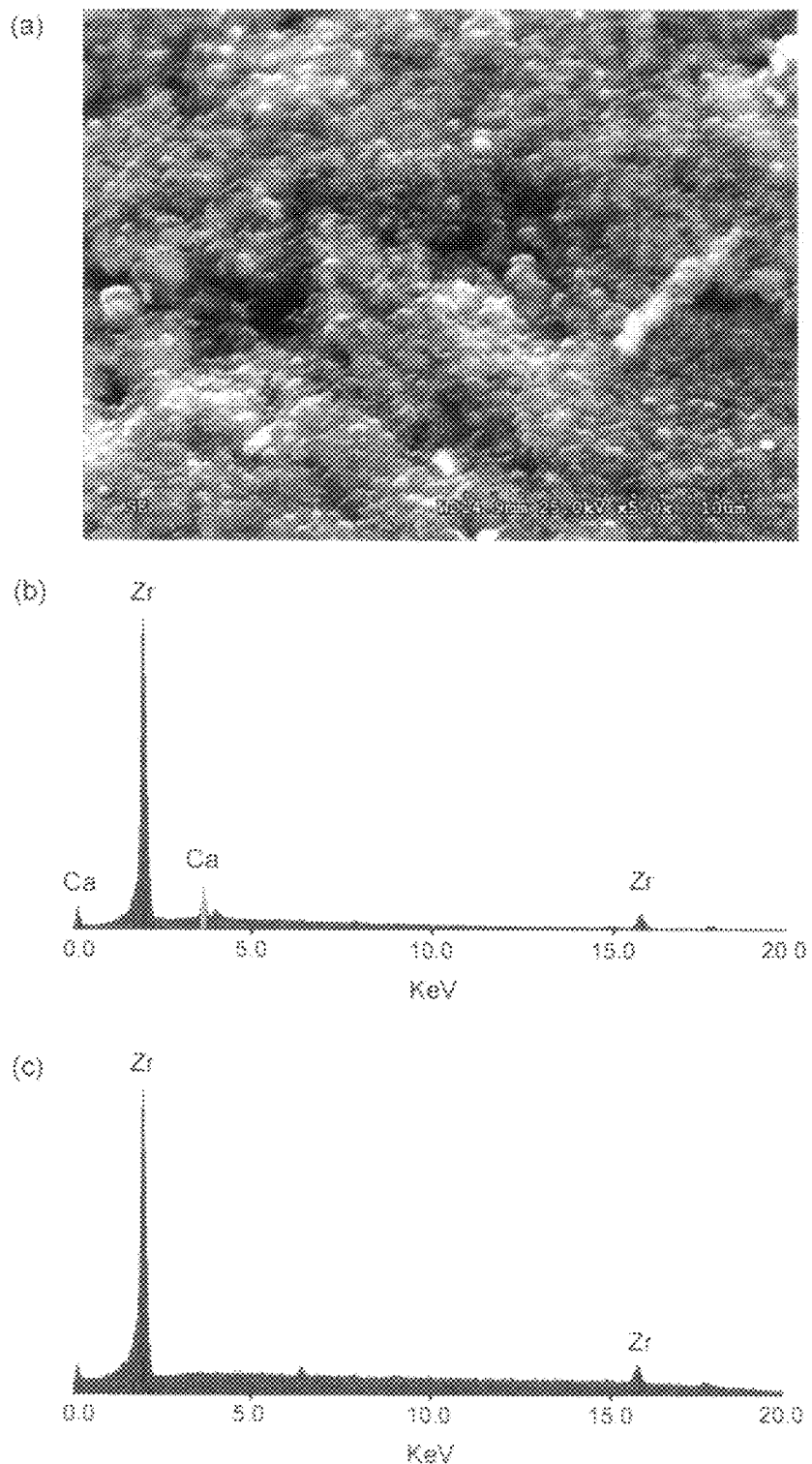
FIG. 3 shows (a) a SEM of CPG coated fully sintered Y-TZP surface, revealing the CPG coating layer with a rough surface morphology. A powdered CPG slurry was applied to the dense Y-TZP surface and then subjected to microwave sintering for 5 minutes; (b) An energy dispersive X-ray spectrum collected from the surface of a CPG coated Y-TZP, revealing an elemental composition containing both Ca and Zr; and (c) An energy dispersive X-ray spectrum collected from the Y-TZP surface before subject to CPG coating, revealing an elemental composition containing predominantly Zr.

The present invention provides a functionally graded CPG/zirconia structure by infiltrating a low elastic modulus, bioactive CPG into the surface of a strong, high modulus zirconia. Preliminary studies demonstrated that functionally graded materials (FGMs) can be produced using a CPG formulation (Ca/P ratio 0.6, elastic modulus approximately 45 GPa, melting temperature approximately 1200° C., CTE approximately $110 \times 10^{-7}$ in/in/° C.), infiltrated into the surface of strong yttria-tetragonal zirconia polycrystal (Y-TZP, CTE approximately $105 \times 10^{-7}$ in/in/° C.) (FIG. 2). As can be seen, the surface of the Y-TZP rod consists of a residual CPG layer (~10 μm), a graded CPG/Y-TZP layer (approximately 100 μm), and a dense Y-TZP interior. However, the CTE of this particular CPG composition is not closely matched with that of Y-TZP. Therefore, effort is required to tailor the CPG composition for better matching in CTE with Y-TZP. Finally, the mechanical properties and bioactivity of the novel CPG/Y-TZP structures have yet to be determined.

Previous inventions provided a strong, aesthetic, bioinert graded glass/ceramic/glass composites for next-generation dental crowns and bridges has revealed a significant improvement in flexural strength in graded structures as compared to their monolithic counterparts. For instance, when a Y-TZP plate (1 mm thick) with both of its surfaces graded with a low modulus (E=67 GPa), bioinert but aesthetic glass ceramic (~120 μm thick on each surface), the graded structures exhibit a 20-30% increment in flexural strength coupled with much better optical properties compared to monolithic Y-TZP. (Zhang et al. Graded glass/zirconia/glass structures for damage resistant ceramic dental and orthopedic prostheses. U.S. Provisional Patent Application No. 60/858,234, filed in 2006). Finite Element Analysis of FGMs with an increasing elastic modulus from the bottom surface to interior shows that the maximum tensile stress could be lowered by 20% compared to its bulk ceramic counterpart, even if the graded layer at the ceramic bottom surface is only 0.2 mm thick. (Huang et al., *J Mater Sci Mater Med* 2007, 18(1):57-64). This is because the FGM at the bottom surface spreads the maximum tensile stresses from the surface into the interior. Therefore, we theorize that if the surface of zirconia implants is graded with a lower modulus, bioactive CPG that exhibits a similar CTE to zirconia, the flexural strength of the CPG/zirconia implant will be further improved while providing an osteoconductive coating for rapid osteointegration.

Recent advances in theoretical and experimental work have shown that functionally graded materials with an increasing elastic modulus from the surface to interior provide unprecedented resistance to contact damage (Suresh et al. (2003) U.S. Pat. No. 6,641,893; Suresh et al. (1997) *Acta Materialia* 45(4): 1307-21; Jitcharoen et al. (1998) *Journal of the American Ceramic Society* 81(9): 2301-8; Suresh et al. (1999) *Acta Materialia* 47(14): 3915-3926). Such damage resistance cannot be realized with conventional homogeneous materials. FGMs are made of two materials that are combined so that the surface of the FGM is composed entirely of material A, and the interior is composed entirely of material B. Additionally, there is a continuous change in the relative proportions of the two materials from the surface to interior. One known FGM is a thick ceramic block, alumina or silicon nitride, infiltrated with a low elastic modulus aluminosilicate glass or oxynitride glass (SiAlYON), respectively, on one surface to produce a graded glass/ceramic (G/C) structure that suppresses contact damage at the top, contact surface (Jitcharoen et al. (1998) *Journal of the American Ceramic Society* 81(9): 2301-8). However, upon infiltration of dense ceramics, the glass penetrates the grain boundaries and grain boundary triple junctions, and as a result, the ceramic grains gradually separate. This leads to an increase in volume at the surface of graded structure and is accompanied by warpage or bending of the specimens where the glass-impregnated surface is convex.

The sliding contact damage resistance of a functionally graded glass/Y-TZP/glass (G/Z/G) composite and its monolithic Y-TZP counterpart were compared. In the G/Z/G system, presintered Y-TZP plates were infiltrated with a low modulus (E=67 GPa), bioinert but aesthetic glass ceramic at both the top and bottom planner surfaces. (Zhang et al., Graded glass/zirconia/glass structures for damage resistant ceramic dental and orthopedic prostheses. U.S. Prov. Patent App. No. 60/858,234, 2006) Excess glass on the G/Z/G surfaces was carefully removed by polishing using 6 μm diamond abrasives, followed by 1 μm finish. The resultant G/Z/G structure was approximately 1.5 mm thick with both of its surfaces consisting of a graded glass-Y-TZP layer (~120 μm). Monolithic Y-TZP plates (1.5 mm thick) with both the top and bottom planner surfaces polished to 1 μm finished were prepared as controls. Frictional sliding was made on the polished planar surfaces of the elastically graded G/Z/G composites and monolithic Y-TZP controls in room temperature water using a spherical tungsten carbide (WC) indenter (r=1.5 mm) mounted onto a mouth-motion simulator (Elf 3300, EnduraTEC Division of Bose, Minnetonka, Minn.). The findings showed the critical normal contact load to initiate the "herringbone" cracks at the contact surface was 600 N for monolithic Y-TZP and 2000 N for graded G/Z/G structures. The "herringbone" cracks are a product of frictional sliding wear, which is a common wear mechanics observed in dental and orthopedic prostheses. The graded G/Z/G composite exhibited a much improved resistance to the sliding contact compared to monolithic Y-TZP. The critical load for the onset of the "herringbone" cracks in G/Z/G was over a factor of 3 higher than that for monolithic Y-TZP.

Y-TZP may undergo hydrothermal degradation or aging in long-term biomedical applications. Ageing of tetragonal zirconia ceramics occurs by a slow phase transformation process—a 'natural' return back to the stable monoclinic phase—in the presence of water or water vapor. (Kobayashi et al., *Solid State Ionics* 1981, 3-4(August):489-493). It is well established that when Y-TZP is in contact with water or body fluid, transformation occurs by a nucleation and growth process, which initiates from isolated surface grains and gradually spreads along the surface and proceeds into the bulk, resulting in surface roughening and reductions in strength, toughness and density. (Hirano, *British Ceramic Transactions and Journal* 1992, 91(5):139-147; Piconi et al., *Biomaterials* 1999, 20(1):1-25; Zhang et al., *Journal of Biomedical Materials Research* 2004, 71B(1): 166-71). The new CPG/Y-TZP composite has a residual CPG layer at its surface, which could impede water absorption and prevent ageing of interior Y-TZP. (Piascik et al., *Journal of Vacuum Science & Technology A* 2006, 24(4):1091-1095).

Functionally graded materials (FGMs) are a new generation of engineered materials wherein the microstructural details are spatially varied, resulting in unprecedented functions and properties that otherwise cannot be realized in conventional homogeneous materials. In some embodiments, the present invention features a functionally graded composite consisting of a bioactive calcium phosphate-based glass (CPG) surface with a gradual transition to a strong zirconia interior. The invention provides a functionally graded CPG/zirconia system for next-generation, strong, bioactive ceramic implants and scaffolds for medical and dental applications.

Functionally graded materials (FGMs) offer unprecedented properties that otherwise cannot be realized in conventional homogeneous materials. In FGMs, two materials are combined so that the surface is all material A, the interior is all material B, and there is a continuous change in the relative proportions of the two materials from the surface to interior. FGMs are of immense interest to industries and defense agencies, so the technology is rapidly advancing. The present invention provides a functionally graded implant device consisting of a bioactive calcium phosphate-based glass surface with a gradual transition to a strong zirconia or zirconia-alumina composite interior. Such a device would be a significant improvement over both metallic and current ceramic implant systems. The compositions of the present invention may be used in next-generation, strong ceramic implants and scaffolds for medical and dental applications, foreshadowing an array of engineering applications, including thermal barrier coatings, cutting tools, and others.

The present invention takes advantage of infiltrating a bioactive, low elastic modulus calcium phosphate glass (CPG) into the surface of a strong, high modulus zirconia or zirconia-alumina composite to produce a functionally graded CPG/zirconia structure. The graded strong, bioactive CPG/zirconia structure offers rapid bone integration, expanding the biomedical applications of ceramics. The immediate objective is to fabricate and validate the bioactivity and mechanical properties of graded CPG/zirconia structures. The compositions of the present invention provide strong, bioactive, graded CPG/zirconia systems for such applications as dental implants, immediate tooth replacement, endodontic posts, orthopedic prostheses, orthopedic stems, bone substitutes, bone screws, plates, and anchors, nonunion fractures repair, alveolar ridge augmentation, missing small bone parts (e.g. fingers, toes, etc), maxilla facial reconstruction, spinal fusion, and scaffolds for bone regeneration foreshadowing other engineering applications.

While the present invention is set forth in description of specific embodiments thereof, it is understood that numerous variations of the invention are enabled and described to those of ordinary skill in the art. Such variations are intended within the scope of the appended claims.

Example 1

Materials and Methods

A bioactive graded CPG/Y-TZP material will be fabricated using a glass-ceramic infiltration technique. We use the CPG compositions developed by Dr. Racquel LeGeros and coworkers at the New York University, which consist of the following contents: CaO, $CaF_2$, $P_2O_5$, MgO and ZnO. (LeGeros, *Journal of Materials Science* 2004, 39(16-17): 5577-5579). The typical CTE value of the bioactive CPGs ranges from 70 to $140 \times 10^{-7}$ in/in/° C., depending on its composition. Therefore, it is possible to develop CPG compositions with CTE values similar to zirconia or alumina or zirconia-alumina composites. Theoretical calculation based on glass expansion factors indicates that a Ca/P ratio between 0.6 and 1.0 are likely to exhibit a desirable CTE value. The selected CPG compositions will be melted at temperatures of approximately 800-1250° C. (depending on the Ca/P ratios) and quenched to room temperature. The as-quenched CPG samples will be attrition milled to reduce the particle size to approximately 10-20 μm. Cylindrical Y-TZP green compacts (approximately 7 mm in diameter and approximately 35 mm long), fabricated from a fine-grain yttria-stabilized zirconia powder (TZ-3Y-E, Tosoh, Japan), will be presintered at temperatures between 900 and 1400° C., creating Y-TZP rods with various porosities. The surface of the presintered Y-TZP will be coated with a powdered CPG slurry (solid loading approximately 10-15 vol %) which has a similar CTE to that of Y-TZP. Glass infiltration and densification will be performed simultaneously at 1450° C. for 2 hrs inside a high temperature box air furnace (ST-1700C-6612, Sentro Tech Corp, Berea, Ohio). A heating and cooling rate of 900° C. per hour will be employed. The thickness of the graded layer may be controlled by the porosity of the presintered Y-TZP. Fabricated CPG/Y-TZP structures will be sectioned and polished for microstructure examination using combined optical and scanning electron microscopy (SEM). The chemical composition of the CPG/Y-TZP graded structure will be determined using energy dispersive X-ray (EDX) analysis. Note, the presintered substrate here may be Y-TZP, Ce-TZP or Mg-PSZ or Ca-PSZ or alumina or zirconia-alumina composite. The CTE of the bioactive glass composition will be selected to match that of substrate material. The infiltration/densification temperatures/time and the heating/cooling rates will be altered accordingly.

Example 2

Materials and Methods

A bioactive graded CPG/Y-TZP material may be made using a solution-precipitation method followed by a glass-ceramic infiltration technique. Cylindrical Y-TZP green compacts (approximately 7 mm in diameter and approximately 35 mm long), fabricated from a fine-grain yttria-stabilized zirconia powder (TZ-3Y-E, Tosoh, Japan), will be presintered at temperatures between 900 and 1400° C., creating Y-TZP rods with various porosities. Partially sintered zirconia rods will be immersed in solutions containing Ca, P, optionally one or more other ions such as Mg, Zn, K, optionally F, and optionally Zr. Precipitation of CPG-based composition to the accessible surface of presintered Y-TZP rods will be performed at room temperature or in a conventional oven at 60° C. or 200° C. for various durations. In addition, microwave heating will be used to facilitate the precipitation process. Infiltration of the CPG-based composition into the Y-TZP and densification of the presintered Y-TZP will be achieved by sintering at 1450° C. for 2 hours. The presintered substrate may be Y-TZP, but Ce-TZP or Mg-PSZ or Ca-PSZ or alumina or zirconia-alumina composite may also be used. The CTE of the bioactive glass composition will be selected to match that of the substrate material. The infiltration/densification temperatures/time and the heating/cooling rates will be altered according to the substrate material.

Example 3

Materials and Methods

A bioactive graded CPG/Y-TZP material may be made using a glass-ceramic infiltration technique of a dense Y-TZP. Dense Y-TZP will be either coated with a powdered CPG-based slurry or deposited with a CPG-based composition using techniques, glass compositions, and precipitation conditions described in Examples 1 and 2. The CTE of the bioactive glass composition is substantially the same as the CTE of the substrate material (i.e. Y-TZP or Ce-TZP or Mg-PSZ or Ca-PSZ or alumina or zirconia-alumina composites). Infiltrating the CPG-based composition into the dense Y-TZP substrate will be performed in one or more firing cycles at a temperature of from about 750° C. to 1000° C. The dense ceramic substrate may be Y-TZP, Ce-TZP, Mg-PSZ or Ca-PSZ or alumina or zirconia-alumina composites. The CTE of the bioactive glass composition will be selected to match that of the substrate material. The infiltration temperatures/time and the heating/cooling rates will be altered according to the substrate material.

The dependence of elastic modulus gradation on the depth (from the surface to interior) will be determined using a nanoindentation technique. The strength of the CPG/Y-TZP rods will be measured using a 3-point bend test along with the reference monolithic Y-TZP rods. The bioactivity of the CPG/Y-TZP composites will be determined by immersing the specimens (4.5 mm in diameter and 25 mm long) in simulated body fluid (SBF) or fetal bovine serum (FBS) at 37° C. for one week. Monolithic Y-TZP rods of the same dimension will be used as controls. The specimen surface, both before and after BSF or FBS exposure, will be coated with a thin carbon layer and examined by SEM. Bioactivity will be determined based on the formation of HA crystals on CPG surfaces. Osteoblast cell response of the CPG/Y-TZP composites will be examined in relation to the monolithic Y-TZP. Animal studies will be conducted to examine to bioactivity of the CPG/Y-TZP composites. A 1-sample t-test will be used for statistical analysis.

Results

A functionally graded CPG/Y-TZP implant with improved bioactivity and strength will be produced. Graded layers with substantially even thickness will be produced on the surface of dense ceramics. The graded CPG/ceramic structures will possess better bioactivity and contact and flexural damage resistance than homogeneous Y-TZP ceramics. The compositions will serve as a basis for developing next-generation longer lasting, better performing zirconia-based FGMs implants and scaffolds for dental, orthopedic, and facial reconstructions, as well as an array of engineering applications, including thermal barrier layers, cutting tools, and others.

We claim:

1. A functionally graded bioactive glass composition/ceramic composite structure or a bioactive glass composition/ceramic/bioactive glass composition sandwich structure comprising a residual bioactive glass composition or glass-ceramic layer and an underlying graded glass-ceramic layer and a dense interior ceramic wherein the bioactive glass composition is a calcium phosphate glass (CPG) consisting of $CaO$, $P_2O_5$, with or without $MgO$, with or without $ZnO$, with or without $K_2O$, with or without $CaF_2$, and with or without Zirconia wherein the graded glass-ceramic layer is 50-500 microns thick.

2. A functionally graded bioactive glass composition/ceramic composite or a bioactive glass composition/ceramic/bioactive glass composition sandwich structure in accordance with claim 1, wherein the interior ceramic comprises yttria-tetragonal zirconia polycrystal (Y-TZP) or ceria stabilized tetragonal zirconia polycrystal (Ce-TZP) or magnesia stabilized zirconia (Mg-PSZ) or calcia stabilized zirconia (Ca-PSZ) or alumina or zirconia-alumina composites.

3. A functionally graded bioactive glass composition/ceramic composite structure or a bioactive glass composition/ceramic/bioactive glass composition sandwich structure according to claim 1 wherein the graded glass-ceramic layer is 50-250 microns thick.

4. A functionally graded bioactive glass composition/ceramic composite structure or a bioactive glass composition/ceramic/bioactive glass composition sandwich structure according to claim 1 wherein the graded glass-ceramic layer is 75-150 microns thick.

5. A method for preparing a functionally graded bioactive glass/ceramic structure or bioactive glass/ceramic/bioactive glass structure according to claim 1 comprising:
   (a) applying a powdered bioactive glass composition to the surface of a presintered (partially sintered) ceramic substrate thereby substantially covering the substrate surface; and
   (b) infiltrating the bioactive glass composition into and densifying the substrate by heating the assembly to at least the sintering temperature of said substrate, to thereby form a functionally graded bioactive glass/ceramic composite or bioactive glass/ceramic/bioactive glass structure consisting of an outer residual glass layer, a graded glass-ceramic layer, and a dense interior ceramic.

6. A method according to claim 5 wherein the glass of the composition has a coefficient thermal expansion (CTE) approximately matching that of the substrate material.

7. A method according to claim 5, wherein the substrate comprises one or more selected from the group consisting of yttria-tetragonal zirconia polycrystal (Y-TZP), ceria stabilized tetragonal zirconia polycrystal (Ce-TZP), magnesia stabilized zirconia (Mg-PSZ), calcia stabilized zirconia (Ca-PSZ), alumina and zirconia-alumina composites.

8. A method according to claim 5, wherein the substrate is presintered at temperatures in the range of 900° C. to 1700° C.

9. A method according to claim 5, wherein said infiltrating is performed in a single firing cycle at a temperature in the range of 1300° C. to 1800° C.

10. A method in accordance with claim 5, wherein the bioactive glass composition powder is dispersed in an aqueous based solution.

11. A method according to claim 5, wherein the CTE of the said bioactive glass is closely matched with yttria-tetragonal zirconia polycrystal (Y-TZP) or ceria stabilized tetragonal zirconia polycrystal (Ce-TZP) or magnesia stabilized zirconia (Mg-PSZ) or calcia stabilized zirconia (Ca-PSZ) or alumina or zirconia-alumina composites.

12. A method for preparing a functionally graded bioactive glass/ceramic structure according to claim 1 comprising:
   (a) applying a bioactive glass composition to the surface of a presintered or partially sintered ceramic substrate by soaking a partially dense ceramic substrate in a solution; and
   (b) heating the assembly to at least the sintering temperature of the substrate to thereby infiltrate the bioactive glass composition into and densify the substrate.

13. A method for preparing a functionally graded bioactive glass/ceramic or bioactive glass/ceramic/bioactive glass structure according to claim 1 comprising:
   (a) applying a powdered bioactive glass composition to the surface of a dense zirconia substrate, or applying a bioactive glass composition to the surface of a dense zirconia substrate by soaking a dense zirconia substrate in a solution; and
   (b) performing one or more heating cycles at a temperature between 750° C. and 1400° C., thereby infiltrating the bioactive glass composition into the dense substrate to form a functionally graded bioactive glass/ceramic composite or bioactive glass/ceramic/bioactive glass structure comprising an outer residual glass layer, a graded glass-ceramic layer, and an dense interior ceramic.

* * * * *